United States Patent [19]

Haga et al.

[11] Patent Number: 4,645,761
[45] Date of Patent: Feb. 24, 1987

[54] ORGANOPHOSPHORUS COMPOUNDS AND INSECTICIDAL, MITICIDAL, NEMATICIDAL OR SOIL PESTICIDAL COMPOSITIONS CONTAINING THEM

[75] Inventors: Takahiro Haga, Kusatsu; Tadaaki Toki, Otsu; Toru Koyanagi, Kyoto; Hiroshi Okada, Kusatsu; Kiyomitsu Yoshida, Kusatsu; Osamu Imai, Kusatsu, all of Japan

[73] Assignee: Ishihara Sangyo Kaisha, Ltd., Osaka, Japan

[21] Appl. No.: 810,266

[22] Filed: Dec. 18, 1985

[30] Foreign Application Priority Data

Dec. 27, 1984 [JP] Japan ................. 59-278481

[51] Int. Cl.$^4$ ................... A01N 57/08; C07F 9/65
[52] U.S. Cl. ..................... 514/94; 548/111
[58] Field of Search .................. 548/111; 514/94

[56] References Cited

U.S. PATENT DOCUMENTS 4,237,122  12/1980  Asao et al. ............... 548/111 X

FOREIGN PATENT DOCUMENTS 439306   12/1967  Switzerland .
2025420  1/1980   United Kingdom .

OTHER PUBLICATIONS

Leber, Chemical Abstracts, vol. 69 (1968) 43913s.
Gubnitskaya et al., Chemical Abstracts, vol. 79 (1973) 42410v.
Myl'nikova et al., Chemical Abstracts, vol. 92 (1980) 94307e.
Myl'nikova et al., Chemical Abstracts, vol. 93 (1980) 186,244f.

Primary Examiner—Richard L. Raymond
Attorney, Agent, or Firm—Oblon, Fisher, Spivak, McClelland & Maier

[57] ABSTRACT

An organophosphorus compound having the formula:

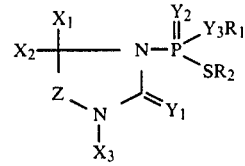

wherein each of $X_1$, $X_2$ and $X_3$ is a hydrogen atom; an alkyl, alkoxy or alkenyl group which may be substituted by halogen, alkoxy, alkylthio, cycloalkyl or phenyl; a phenyl group which may be substituted by halogen; or a cycloalkyl group, each of $Y_1$, $Y_2$ and $Y_3$ is an oxygen atom or a sulfur atom, Z is a carbonyl group; or a methylene group which may be substituted by a cycloalkyl group, by a phenyl group which may be substituted by halogen, or by an alkyl, alkoxy or alkenyl group which may be substituted by halogen, alkoxy alkylthio, cycloalkyl or phenyl, and each of $R_1$ and $R_2$ is an alkyl group which may be substituted by halogen, alkoxy or alkylthio.

23 Claims, No Drawings

ORGANOPHOSPHORUS COMPOUNDS AND INSECTICIDAL, MITICIDAL, NEMATICIDAL OR SOIL PESTICIDAL COMPOSITIONS CONTAINING THEM

The present invention relates to novel organophosphorus compounds having insecticidal, miticidal, nematicidal and soil pesticidal activities. More particularly, the present invention relates to organophosphorus compounds containing a substituted 2-oxoimidazolidine ring, a substituted 2-thioxoimidazolidine ring, a substituted 2,4-dioxoimidazolidine ring or a substituted 4-oxo-2-thioxoimidazolidine ring with a phosphate compound bonded to the nitrogen atom at the 1-position; a process for preparing such organophosphorus compounds; insecticidal, miticidal, nematicidal or soil pesticidal compositions containing such organophosphorus compounds as active ingredients; and an insecticidal, miticidal, nematicidal or soil pesticidal method for the application of such phosphorus compounds.

The organophosphorus compounds of the present invention containing a substituted 2-oxoimidazolidine ring, a substituted 2-thioxoimidazolidine ring, a substituted 2,4-dioxoimidazolidine ring or a substituted 4-oxo-2-thioxoimidazolidine ring with a phosphate compound bonded to the nitrogen atom at the 1-position, are novel.

On the other hand, Swiss Pat. No. 439,306 discloses a process for the preparation of N-phosphoroamidates of substituted 2-thioxoimidazolidines. However, the disclosed compounds are different in their chemical structure from the compounds of the present invention. This reference discloses that the compounds obtained by the process are effective against microorganisms harmful to plants (namely, they have fungicidal activities). However, there is no disclosure which indicates or suggests that they are effective against insects, mites, nematodes or soil pests in the sense of the present invention.

The present invention provides novel organophosphorus compounds having the following formula I, which include stereoisomers such as optical isomers:

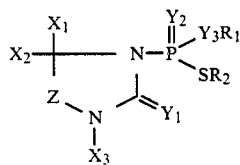

wherein each of $X_1$, $X_2$ and $X_3$ is a hydrogen atom; an alkyl, alkoxy or alkenyl group which may be substituted by halogen, alkoxy, alkylthio, cycloalkyl or phenyl; a phenyl group which may be substituted by halogen; or a cycloalkyl group, each of $Y_1$, $Y_2$ and $Y_3$ is an oxygen atom or a sulfur atom, Z is a carbonyl group; or a methylene group which may be substituted by a cycloalkyl group, by a phenyl group which may be substituted by halogen, or by an alkyl, alkoxy or alkenyl group which may be substituted by halogen, alkoxy, alkylthio, cycloalkyl or phenyl, and each of $R_1$ and $R_2$ is an alkyl group which may be substituted by halogen, alkoxy or alkylthio.

The present invention also provides a process for preparing the compounds of the formula I, which comprises reacting a heterocyclic compound having the formula:

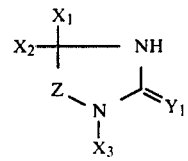

wherein $X_1$, $X_2$, $X_3$, $Y_1$ and Z are as defined above, with a compound having the formula:

wherein Hal is a halogen atom, and $Y_2$, $Y_3$, $R_1$ and $R_2$ are as defined above, in the presence of an acid-acceptor.

Further, the present invention provides an insecticidal, miticidal, nematicidal or soil pesticidal composition comprising an insecticidally, miticidally, nematicidally or soil pesticidally effective amount of an organophosphorus compound of the formula I and, if necessary, a carrier.

Furthermore, the present invention provides an insecticidal, miticidal, nematicidal or soil pesticidal method, which comprises applying an insecticidally, miticidally, nematicidally or soil pesticidally effective amount of an organophosphorus compound of the formula I to a site to be protected from insects, mites, nematodes or soil pests.

Now, the present invention will be described in detail with reference to the preferred embodiments.

In the formula I, the alkyl group or the alkyl moiety of the alkoxy group or the alkyl moiety of the alkylthio group involved in $X_1$, $X_2$, $X_3$, Z, $R_1$ and $R_2$, is preferably an alkyl group having from 1 to 6 carbon atoms such as methyl, ethyl, propyl, butyl, pentyl or hexyl. The alkenyl group involved in $X_1$, $X_2$, $X_3$ and Z is preferably an alkenyl group having from 2 to 6 carbon atoms such as ethenyl, propenyl, butenyl, pentenyl or hexenyl. The cycloalkyl group involved in $X_1$, $X_2$, $X_3$ and Z is preferably a cycloalkyl group having from 3 to 6 carbon atoms such as cyclopropyl, cyclobutyl, cyclopentyl or cyclohexyl. As the halogen atom involved in $X_1$, $X_2$, $X_3$, Z, $R_1$ and $R_2$, there may be mentioned fluorine, chlorine, bromine or iodine.

Among the substituents for $X_1$ and $X_2$, a hydrogen atom, an alkyl group or an alkoxy group is preferred. Likewise, among the substituents for $X_3$, a hydrogen atom; an alkyl or alkoxy group which may be substituted by phenyl; or a cycloalkyl group is preferred. More preferred is a hydrogen atom, an alkyl group or a cycloalkyl group, and the most preferred is an alkyl group. Among the substituents for $Y_1$, $Y_2$ and $Y_3$, an oxygen atom is preferred. Among the substituents for Z, a carbonyl group is preferred. Among the substituents for $R_1$ and $R_2$, an alkyl group is preferred. Further, the substituents for $R_1$ and $R_2$ are preferably different from each other. Namely, preferred is a case where $R_1$ is methyl or ethyl, whereas $R_2$ is n-propyl, isopropyl, n-butyl, sec-butyl, isobutyl or tert-butyl. More preferred is a case where $R_1$ is ethyl, whereas $R_2$ is n-propyl or sec-butyl.

The compounds of the formula I of the present invention may be prepared by e.g. the following process:

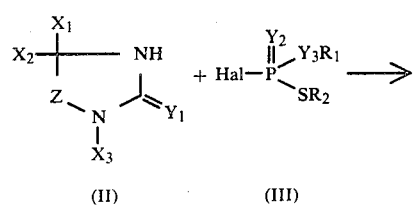 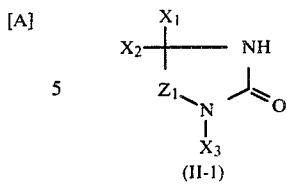 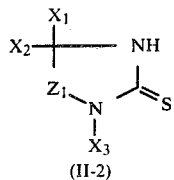

[A]

(II)  (III)

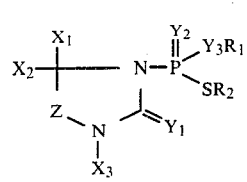 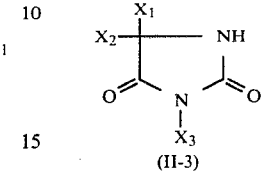 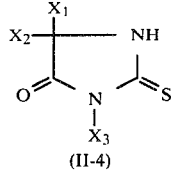

(II-1)   (II-2)

and (II-3)   (II-4)

may be prepared by the following processes C, D, E and F.

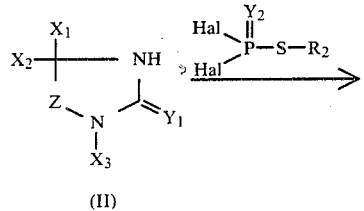

(I)

[B]

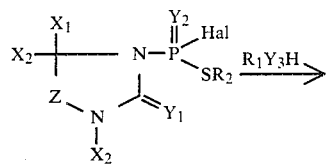

(II)

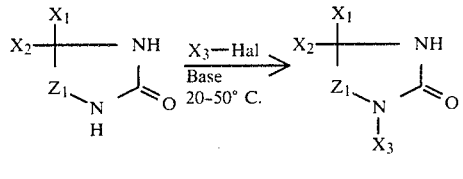

[C]

(II-1)

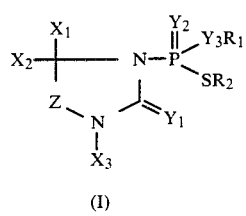

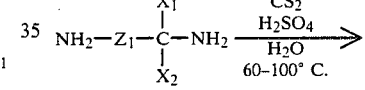

[D]

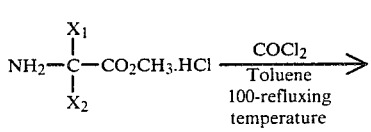

(II-2)

(I)

wherein Hal is a halogen atom, and $X_1$, $X_2$, $X_3$, $Y_1$, $Y_2$, $Y_3$, Z, $R_1$ and $R_2$ are as defined above.

The above reaction is usually conducted within a temperature range of from $-100°$ to $50°$ C., preferably from $-80°$ C. to room temperature ($30°$ C.).

This reaction is conducted in the presence of an acid-acceptor. As the acid-acceptor, there may be mentioned an organic lithium compound such as n-butyl lithium, tert-butyl lithium or phenyl lithium; an inorganic base such as sodium hydroxide, potassium hydroxide, sodium hydride or potassium hydride; or an organic base such as triethylamine or pyridine. Further, the reaction is preferably conducted in a solvent. As the solvent, there may be mentioned an aromatic hydrocarbon such as benzene, toluene, xylene or chlorobenzene; a cyclic or non-cyclic aliphatic hydrocarbon such as hexane or cyclohexane; an ether such as diethyl ether, methyl ethyl ether, dioxane or tetrahydrofuran; a nitrile such as acetonitrile, propionitrile or acrylonitrile; or an aprotic polar solvent such as dimethylformamide, dimethylsulfoxide, sulfolane or hexamethylphosphoric triamide.

Among the starting materials of the formula II, the compounds having the formulas:

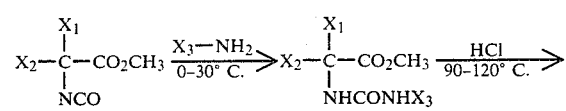

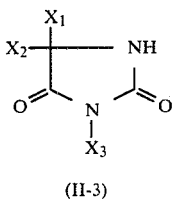

(II-3)

[E]

[F]

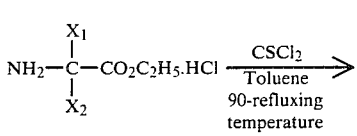

-continued

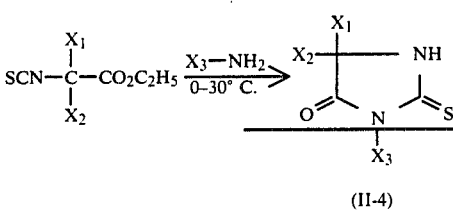
(II-4)

In the above formulas, Hal is a halogen atom, $X_1$, $X_2$ and $X_3$ are as defined above, and $Z_1$ is a methylene group which may be substituted by a cycloalkyl group, by a phenyl group which may be substituted by halogen, or by an alkyl, alkoxy or alkenyl group which may be substituted by halogen, alkoxy, alkylthio, cycloalkyl or phenyl.

The reaction conditions for the respective reactions for the preparation of the starting materials, such as the reaction temperature, the reaction time, the solvent optionally employed or the base, may suitably be selected from the reaction conditions for the conventional reactions of similar types.

Typical examples of the starting compounds prepared by the above-mentioned processes C, D, E and F will be given in Table 1.

TABLE 1

| $X_1$ | $X_2$ | $X_3$ | $Y_1$ | $Z$ | Physical properties (Melting point) |
|---|---|---|---|---|---|
| H | H | ▷ | O | CO | 119–124° C. |
| H | H | $CH_2=CH-CH_2-$ | O | CO | 66–68° C. |
| H | H | $CH_3O$ | O | CO | 98–107° C. |
| H | H | ⌬ (phenyl) | $CH_3$ | O | CO | 156–159° C. |
| H | H | H | S | $CH_2$ | 197–198° C. |
| $CH_3$ | $CH_3$ | H | O | CO | 170–171° C. |
| $CH_3$ | $CH_3$ | H | S | CO | 138–140° C. |
| $CH_3$ | $C_2H_5$ | H | O | CO | 145–146° C. |
| ▷ | H | $CH_3$ | O | CO | — |
| $CH_3SCH_2$ | H | H | O | CO | — |
| $CF_2H$ | H | H | O | CO | — |
| $CH_3OCH_2$ | H | H | O | CO | 100–101° C. |
| $CH_3$ | H | $CH_3$ | S | CO | 138–140° C. |
| H | H | $CH_3$ | O | $CH_3OCH_2$ | — |
| H | H | 2,4-Cl$_2$-C$_6$H$_3$ | O | CO | 197–199° C. |
| H | H | iso-$C_3H_7$ | O | CO | 87–89° C. |
| $C_2H_5$ | H | $CH_3$ | O | CO | 100.5–101° C. |
| $CH_3$ | $CH_3$ | $C_2H_5$ | O | CO | 97–98° C. |
| $CH_3$ | H | $CH_3$ | O | CO | 111–112° C. |
| H | H | $CH_3$ | S | CO | 160–163° C. |
| $ClCH_2CH_2CH_2-$ | H | $CH_3$ | O | CO | 92–94° C. |

Now, the present invention will be described in further detail with reference to Examples. However, it should be understood that the present invention is by no means restricted by these specific Examples.

SYNTHETIC EXAMPLE 1

Preparation of S-sec-butyl O-ethyl (3-methoxy-2,4-dioxo-1-imidazolidinyl)phosphonothiolate (1) An aqueous solution prepared by dissolving 3.34 g of hydroxylamine methyl ether hydrochloride in 20 ml of water, was cooled with ice. While stirring the solution, an aqueous solution prepared by dissolving 2.24 g of potassium hydroxide in 20 ml of water, was gradually dropwise added thereto. After completion of the dropwise addition, the reaction system was returned to room temperature and the stirring was continued for 1 hour. Then, the reaction mixture was again cooled with ice, and 2.58 g of ethyl isocyanatoacetate was gradually added. The reaction system was returned to room temperature, and the reaction solution was stirred at a temperature of from 40° to 50° C. for further 0.5 hour. Then, the reaction solution was cooled with ice, and 10 ml of 6N hydrochloric acid was added. The mixture was refluxed for 3 hours, and then cooled with ice, whereby crystals precipitated. The crystals were collected by filtration to obtain 1.8 g of 3-methoxy-2,4-dioxoimidazolidine having a melting point of from 98° to 107° C.

(2) A solution prepared by suspending 0.6 g of 60% sodium hydride (dispersion in mineral oil) in 10 ml of tetrahydrofuran, was cooled with ice, and while stirring the solution, 1.3 g of 3-methoxy-2,4-dioxoimidazolidine obtained in the above step (1) was gradually added in its solid state to the solution. Then, the reaction solution was left to return to room temperature, then stirred for 2 hours and again cooled with ice. A solution prepared by dissolving 2.6 g of S-sec-butyl O-ethyl phosphorochloridothiolate in 5 ml of tetrahydrofuran, was added thereto, and the mixture was stirred overnight at room temperature to complete the reaction.

After completion of the reaction, 20 ml of tetrahydrofuran was added to the reaction mixture, and insoluble matters were removed by filtration. The filtrate was concentrated under reduced pressure. Then, the residue was purified by silica gel column chromatography to obtain 0.42 g of S-sec-butyl O-ethyl (3-methoxy-2,4-dioxo-1-imidazolidinyl)phosphonothiolate having a refractive index of 1.5050 (at 20.8° C.).

SYNTHETIC EXAMPLE 2

Preparation of S-sec-butyl O-ethyl (5-sec-butyl-3-methyl-2,4-dioxo-1-imidazolidinyl)phosphonothiolate A solution prepared by dissolving 2 g of 5-sec-butyl-3-methyl-2,4-dioxoimidazolidine in 20 ml of tetrahydrofuran, was cooled with ice, and 0.5 g of a nujor mixture of 60% sodium hydride (dispersion in mineral oil) was gradually added thereto while maintaining the reaction system at a temperature of from 0° to 5° C. After the addition, the reaction solution was returned to room temperature, then stirred for 20 minutes and again cooled with ice. Then, a solution prepared by dissolving 2.9 g of S-sec-butyl O-ethyl phosphorochloridothiolate in 5 ml of tetrahydrofuran, was gradually dropwise added while maintaining the reaction system at a temperture of from 0° to 5° C. After completion of the dropwise addition, the reaction solution was returned to room temperature, and stirred for 2 hours to complete the reaction.

After completion of the reaction, the reaction mixture was poured into a saturated sodium chloride aqueous solution, and extracted with ethyl acetate The extract was dried over anhydrous sodium sulfate, and the solvent was distilled off under reduced pressure. The residue was purified by silica gel column chromatography to obtain 1.11 g of S-sec-butyl O-ethyl (5-sec-butyl-3-methyl-2,4-dioxo-1-imidazolidinyl)phosphonothiolate having a refractive index of 1.4945 (at 21.7° C.) and 760 mg of a diastereomer having a refractive index of 1.4968 (at 21.6° C.).

SYNTHETIC EXAMPLE 3

Preparation of O-ethyl S-n-propyl (3-methyl-2-oxo-1-imidazolidinyl)phosphonothiolate 520 mg of 1-methyl-2-oxoimidazolidine was dissolved in 15 ml of tetrahydrofuran, and after flushing with nitrogen, the reaction system was cooled to −78° C. with dry ice. While stirring the solution, 3.4 ml of a n-hexane solution of butyl lithium (1.55 M) was gradually dropwise added at the same temperature. After completion of the dropwise addition, the mixture was stirred at the same temperature for 20 minutes. Then, a solution prepared by dissolving 1.6 g of O-ethyl S-n-propyl phosphorochloridothiolate in 3 ml of tetrahydrofuran, was gradually dropwise added thereto. After completion of the dropwise addition, the reaction solution was returned to room temperature, and then stirred for 2 hours to complete the reaction.

After completion of the reaction, the reaction mixture was poured into water, and extracted twice with ethyl acetate. The organic layer was washed with a saturated sodium chloride aqueous solution, and dried over anhydrous sodium sulfate. Then, the solvent was distilled off under reduced pressure, and the residue was purified by silica gel column chromatography to obtain 300 mg of O-ethyl S-n-propyl (3-methyl-2-oxo-1imidazolidinyl)phosphonothiolate having a refractive index of 1.5088 (at 18.8° C.).

SYNTHETIC EXAMPLE 4

Preparation of S-sec-butyl O-ethyl (3-methyl-2,4-dioxo-1-imidazolidinyl)phosphonothiolate A solution prepared by dissolving 1.0 g of 3-methyl-2,4-dioxoimidazolidine in 50 ml of tetrahydrofuran, was cooled to −78° C. with dry ice, and 5.66 ml of a n-hexane solution of n-butyl lithium (1.55 M), was added thereto. The mixture was stirred at the same temperature for 10 minutes, and then a solution prepared by dissolving 2.28 g of S-sec-butyl O-ethyl phosphorochloridothiolate in 3 ml of tetrahydrofuran, was gradually dropwise added thereto. After completion of the dropwise addition, the reaction solution was returned to room temperature, and stirred for further 3.5 hours to complete the reaction.

After completion of the reaction, the reaction mixture was poured into water and extracted with ethyl acetate. The extract was washed with a saturated sodium chloride aqueous solution, and dried over anhydrous sodium sulfate. Then, the solvent was distilled off under reduced pressure, and the residue was purified by silica gel column chromatography to obtain 1.55 g of S-sec-butyl O-ethyl (3-methyl-2,4-dioxo-1-imidazolidinyl) phosphonothiolate having a refractive index of 1.5079 (at 25.8° C.).

SYNTHETIC EXAMPLE 5

Preparation of S-sec-butyl O-ethyl (3,5-dimethyl-2,4-dioxo-1-imidazolidinyl)phosphonothiolate A solution prepared by dissolving 2.18 g of 3,5-dimethyl-2,4-dioxoimidazolidine in 30 ml of tetrahydrofuran, was cooled to −78° C. with dry ice, and 11 ml of a n-hexane solution of n-butyl lithium (1.55 M), was added thereto. The mixture was stirred at the same temperature for 15 minutes, and then a solution prepared by dissolving 3.71 g of S-sec-butyl O-ethyl phosphorochloridothiolate in 3 ml of tetrahydrofuran, was gradually dropwise added thereto. After completion of the dropwise addition, the reaction solution was returned to room temperature, and stirred for further 3 hours to complete the reaction.

After completion of the reaction, the reaction mixture was poured into a saturated sodium chloride aqueous solution, then extracted with ethyl acetate and dried over anhydrous sodium sulfate. Then, the solvent was distilled off under reduced pressure, and the residue was purified by silca gel column chromatography to obtain 3.23 g of S-sec-butyl O-ethyl (3,5-dimethyl-2,4-dioxo-1-imidazolidinyl)phosphonothiolate having a refractive index of 1.5028 (at 23.6° C.).

This compound was further separated by silica gel column chromatography to obtain diastereomers having a refractive index of 1.5022 (at 24.0° C.) and a refractive index of 1.5032 (at 24.0° C.).

SYNTHETIC EXAMPLE 6

Preparation of S-sec-butyl O-ethyl [3-methyl-5-(2-methylthioethyl)-2,4-dioxo-1-imidazolidinyl]phosphonothiolate A solution prepared by dissolving 2.0 g of 3-methyl-5-(2-methylthioethyl)-2,4-dioxoimidazolidine in 30 ml of tetrahydrfuran, was cooled with ice, and 0.44 g of 60% sodium hydride (dispersion in mineral oil), was gradually added thereto. After the addition, the reaction solution was returned to room temperature, stirred for further 1.5 hours, and again cooled with ice. Then, 2.65 g of S-sec-hours, butyl O-ethyl phosphorochloridothiolate was dropwise added. After completion of the dropwise addition, the reaction solution was returned to room temperature, and stirred for further 1.5 hours to complete the reaction.

After completion of the reaction, the reaction mixture was poured into a saturated sodium chloride aqueous solution, and extracted with ethyl acetate. The extract was dried over anhydrous sodium sulfate, and the solvent was distilled off under reduced pressure. The residue was purified by silca gel column chromatography to obtain 1.0 g of S-sec-butyl O-ethyl [3-methyl-5-(2-methylthioethyl)-2,4-dioxo-1-imidazolidinyl]phosphonothiolate having a refractive index of 1.5224 (at 20.8° C.) and 0.58 g of a diastereomer having a refractive index of 1.5233 (at 20.8° C.).

SYNTHETIC EXAMPLE 7

Preparation of S-sec-butyl O-ethyl (2,4-dioxo-1-imidazolidinyl)phosphonothiolate 2 g of 2,4-dioxoimidazolidine was dissolved in a mixed solution of 25 ml of tetrahydrofuran and 6 ml of hexamethylphosphoric triamide, and then cooled with ice. Then, 1.76 g of 60% sodium hydride (dispersion in mineral oil) was gradually added thereto while maintaining the reaction system at a temperature of from 0° to 5° C. After the addition, the reaction solution was returned to room temperature and stirred for 20 minutes. Then, the reaction solution was cooled again with ice, and a solution prepared by dissolving 4.8 g of S-sec-butyl O-ethyl phosphorochloridothiolate in 5 ml of tetrahydrofuran, was gradually dropwise added thereto while maintaining the reaction system at a temperature of from 0° to 5° C. After completion of the dropwise addition, the reaction solution was gradually returned to room temperature, and stirred for further 2 hours to complete the reaction.

After completion of the reaction, the reaction mixture was poured into ice water, and the pH was adjusted to 7 with concentrated hydrochloric acid. The reaction mixture was extracted a few times with ethyl acetate. Then, the organic layer was washed with a saturated sodium chloride aqueous solution, and dried over anhydrous sodium sulfate. Then, the solvent was distilled off under reduced pressure, and the residue was purified by silica gel column chromatography to obtain 2.2 g of S-sec-butyl O-ethyl (2,4-dioxo-1-imidazolidinyl) phosphonothiolate having a refractive index of 1.5180 (at 21.2° C.).

SYNTHETIC EXAMPLE 8

Preparation of S-sec-butyl O-ethyl (5-allyl-3-methyl-2,4-dioxo-1-imidazolidinyl)phosphonothiolate (1) 5.8 g of N-methylcarbamoyl-α-allylglycine was dissolved in 80 ml of 3N hydrochloric acid, and refluxed for 2.5 hours to complete the reaction.

After completion of the reaction, the reaction mixture was concentrated to a half volume under reduced pressure, and extracted three times with methylene chloride. The extract was dried over anhydrous sodium sulfate, and the solvent was distilled off under reduced pressure to obtain 4.2 g of 5-allyl-3-methyl-2,4-dioxoimidazolidine having a melting point of from 89° to 90° C. as colorless crystals.

(2) 1.6 g of 5-allyl-3-methyl-2,4-dioxoimidazolidine obtained in the above step (1) was dissolved in 25 ml of tetrahydrofuran, and then cooled with ice. Then, 0.5 g of 60% sodium hydride (dispersion in mineral oil) was gradually added thereto while maintaining the reaction system at a temperature of from 0° to 5° C. After the addition, the reaction solution was returned to room temperature, and stirred for 15 minutes. Then, the solution was cooled again with ice, and a solution prepared by dissolving 2.5 g of S-sec-butyl O-ethyl phosphorochloridothiolate in 5 ml of tetrahydrofuran, was gradually dropwise added thereto while maintaining the reaction system at a temperature of from 0° to 5° C. After completion of the dropwise addition, the solution was gradually returned to room temperature, and stirred for further 5 hours to complete the reaction.

After completion of the reaction, the reaction mixture was adjusted to pH 7 with concentrated hydrochloric acid, and concentrated to a ⅓ volume under reduced pressure. Then, 100 ml of methylene chloride was added thereto, and the mixture was washed twice with a saturated sodium chloride aqueous solution and once with a sodium hydrogencarbonate solution, and dried over anhydrous sodium sulfate. Then, the solvent was distilled off under reduced pressure, and the residue was purified by silica gel column chromatography to obtain 1.76 g of S-sec-butyl O-ethyl (5-allyl-3-methyl-2,4-dioxo-1-imidazolidinyl)phosphonothiolate having a refractive index of 1.5039 (at 22.2° C.) and 0.37 g of a diastereomer having a refractive index of 1.5054 (at 22.1° C.).

SYNTHETIC EXAMPLE 9

Preparation of S-sec-butyl O-ethyl (5,5-dimethyl-4-oxo-2-thioxo-1-imidazolidinyl)phosphonothiolate (1) 2.75 g of potassium hydroxide was dissolved in 50 ml of water, and 5.0 g of 2-aminoisobutyric acid and 3.6 g of methyl isothiocyanate were sequentially added thereto. The mixture was stirred at 40° C. for 15 minutes. Then, the reaction mixture was acidified by an addition of concentrated hydrochloric acid, and refluxed for 10 minutes to complete the reaction.

After completion of the reaction, the reaction mixture was cooled with ice, whereby crystals precipitated. The crystals were collected by filtration to obtain 3.0 g of 5,5-dimethyl-4-oxo-2-thioxoimidazolidine having a melting point of from 138 to 140° C.

(2) 1.0 g of 5,5-dimethyl-4-oxo-2-thioxoimidazolidine obtained in the above step (1) was dissolved in 15 ml of tetrahydrofuran, and cooled to −78° C. with dry ice. Then, 4.1 ml of a n-hexane solution of n-butyl lithium (1.55 M) was dropwise added thereto. After completion of the dropwise addition, the mixture was stirred at the same temperature for 10 minutes. Then, 1.82 g of S-sec-butyl O-ethyl phosphorochloridothiolate was dropwise added thereto, and the mixture was returned to room temperature, and stirred for further 3 hours to complete the reaction.

After completion of the reaction, the reaction mixture was poured into a saturated sodium chloride aqueous solution, then extracted with ethyl acetate and dried over anhydrous sodium sulfate. Then, the solution was distilled off under reduced pressure, and the residue was purified by silica gel column chromatography to obtain 0.80 g of S-sec-butyl O-ethyl (5,5-dimethyl-4-oxo-2-thioxo-1-imidazolidinyl)phosphonothiolate having a refractive index of 1.5428 (at 19.6° C.).

SYNTHETIC EXAMPLE 10

Preparation of O-ethyl S-n-propyl (2,4-dioxo-3-methyl-1-imidazolidinyl)phosphonothiolate 1.0 g of 3-methyl-2,4-dioxoimidazolidine was dissolved in 50 ml of tetrahydrofuran, and cooled to −78° C. Then, 5.7 ml of a n-hexane solution of n-butyl lithium (1.55 M) was gradually dropwise added thereto. The reaction solution was stirred at the same temperature for 15 minutes, and then 5 ml of a tetrahydrofuran solution containing 1.95 g of S-sec-butyl O-ethyl phosphorochloridothiolate was gradually dropwise added thereto. After completion of the dropwise addition, the reaction was conducted for 2 hours while gradually returning the solution temperature to room temperature. After completion of the reaction, the reaction solution was poured into water, and extracted with ethyl acetate. The extract was washed with a saturated sodium chloride aqueous solution, and dried over anhydrous sodium sulfate. Then, the solvent was distilled off, and the residue was purified by silica gel column chromatography to obtain 0.82 g of the desired product having a refractive index of 1.5081 (at 33.2° C.) Representative specific compounds of the present invention will be presented in Table 2.

TABLE 2

$$X_2 - \overset{X_1}{\underset{\underset{X_3}{\overset{|}{N}}}{\overset{|}{\underset{}{C}}}} - N - \overset{Y_2}{\underset{Y_1}{\overset{\|}{P}}} \overset{Y_3 R_1}{\underset{SR_2}{}} \quad (I)$$

| Compound No. | X₁ | X₂ | X₃ | Y₁ | Y₂ | Y₃ | Z | R₁ | R₂ | Physical properties (Refractive index) |
|---|---|---|---|---|---|---|---|---|---|---|
| 1 | H | H | CH₃ | O | O | O | CH₂ | C₂H₅ | n-C₃H₇ | $n_D^{18.8}$ 1.5088 |
| 2 | " | " | " | " | " | " | " | " | sec-C₄H₉ | $n_D^{20.8}$ 1.5053 |
| 3 | " | " | " | " | " | " | CO | " | n-C₃H₇ | $n_D^{33.2}$ 1.5081 |
| 4 | " | " | " | " | " | " | " | " | sec-C₄H₉ | $n_D^{25.8}$ 1.5079 |
| 5 | " | " | iso-C₃H₇ | " | " | " | " | " | " | $n_D^{24.6}$ 1.4957 |
| 6 | " | " | " | " | " | " | " | " | 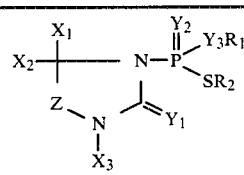 | $n_D^{26.4}$ 1.5563 |
| 7 | C₂H₅ | " | CH₃ | " | " | " | " | " | " | $n_D^{19.6}$ 1.4990 |
| 8 | H | " | " | S | " | " | " | " | " | $n_D^{16.8}$ 1.5623 |
| 9 | CH₃ | CH₃ | " | " | " | " | " | " | " | $n_D^{19.6}$ 1.5428 |
| 10 | " | " | C₂H₅ | O | " | " | " | " | " | $n_D^{19.6}$ 1.4906 |
| 11 | " | C₂H₅ | CH₃ | " | " | " | " | " | " | $n_D^{19.4}$ 1.4948 |
| 12 | H | H | H | " | " | " | " | " | " | $n_D^{21.2}$ 1.5180 |
| 13 | CH₃ | CH₃ | " | " | " | " | " | " | " | $n_D^{19.4}$ 1.4950 |
| 14 | C₂H₅ | " | " | " | " | " | " | " | " | $n_D^{22.4}$ 1.4962 |
| 15 | CH₃ | H | CH₃ | " | " | " | " | " | " | $n_D^{23.6}$ 1.5028 |
| 16 | " | " | " | " | " | " | " | " | " | $n_D^{24.0}$ 1.5022 |
| 17 | " | " | " | " | " | " | " | " | " | $n_D^{24.0}$ 1.5035 |
| 18 | iso-C₃H₇ | " | " | " | " | " | " | " | " | $n_D^{23.8}$ 1.4948 |
| 19 | sec-C₄H₉ | " | " | " | " | " | " | " | " | $n_D^{21.7}$ 1.4945 |
| 20 | " | " | " | " | " | " | " | " | " | $n_D^{21.6}$ 1.4968 |
| 21 | —CH₂CH₂SCH₃ | " | " | " | " | " | " | " | " | $n_D^{20.8}$ 1.5224 |
| 22 | " | " | " | " | " | " | " | " | " | $n_D^{20.8}$ 1.5233 |

TABLE 2-continued

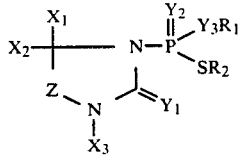

(I)

| Compound No. | X₁ | X₂ | X₃ | Y₁ | Y₂ | Y₃ | Z | R₁ | R₂ | Physical properties (Refractive index) |
|---|---|---|---|---|---|---|---|---|---|---|
| 23 | —⌬ (phenyl) | " | " | " | " | " | " | " | " | $n_D^{20.8}$ 1.5406 |
| 24 | —CH₂—⌬ | " | " | " | " | " | " | " | " | $n_D^{21.4}$ 1.5353 |
| 25 | " | " | " | " | " | " | " | " | " | $n_D^{20.5}$ 1.5340 |
| 26 | H | " | —CH₂—⌬ | " | " | " | " | " | " | $n_D^{20.8}$ 1.5369 |
| 27 | " | " | OCH₃ | " | " | " | " | " | " | $n_D^{20.8}$ 1.5050 |
| 28 | " | " | ▷ (cyclopropyl) | " | " | " | " | " | " | $n_D^{20.8}$ 1.5169 |
| 29 | " | " | —CH₂—CH=CH₂ | " | " | " | " | " | " | $n_D^{20.8}$ 1.5101 |
| 30 | —CH₂CH=CH₂ | " | CH₃ | " | " | " | " | " | " | $n_D^{22.2}$ 1.5039 |
| 31 | " | " | " | " | " | " | " | " | " | $n_D^{22.1}$ 1.5054 |
| 32 | OCH₃ | " | " | " | " | " | " | " | " | $n_D^{16.6}$ 1.5037 |
| 33 | —CH₂CH₂CH₂Cl | " | " | " | " | " | " | " | " | $n_D^{26.1}$ 1.5080 |
| 34 | —CH₂OCH₃ | " | " | " | " | " | " | " | " | $n_D^{20.4}$ 1.5001 |
| 35 | " | " | " | " | " | " | " | " | " | $n_D^{20.5}$ 1.5013 |
| 36 | ▷ | " | " | " | " | " | " | " | " | — |
| 37 | —CH₂—▷ | " | " | " | " | " | " | " | " | — |
| 38 | H | " | " | " | S | " | " | " | n-C₄H₉ | — |
| 39 | " | " | " | " | O | S | " | " | sec-C₄H₉ | — |
| 40 | " | " | " | " | " | O | " | C₂H₄OCH₃ | " | — |
| 41 | " | " | " | " | " | " | " | CH₂CH₂F | " | — |
| 42 | " | " | " | " | " | " | " | C₂H₅ | iso-C₄H₉ | — |
| 43 | " | " | " | " | " | " | " | " | tert-C₄H₉ | — |
| 44 | —CH₂SCH₃ | " | H | " | " | " | " | " | sec-C₄H₉ | — |
| 45 | CHF₂ | " | " | " | " | " | " | " | " | — |
| 46 | —⌬—Cl | " | " | " | " | " | " | " | " | — |
| 47 | —CH₂CH₂CH₂Cl | " | CH₃ | " | " | " | " | " | " | $n_D^{26.5}$ 1.5061 |

Among the representative compounds listed in Table 2, Compounds Nos. 16 and 17, Compounds Nos. 19 and 20, Compounds Nos. 21 and 22, Compounds Nos. 24 and 25, Compounds Nos. 30 and 31, Compounds Nos. 33 and 47, and Compounds Nos. 34 and 35, are diastereomers (due to the asymmetric carbon at the 5-position of the imidazolidine ring and phosphorus atom) to each other, respectively. Compound No. 15 is a mixture of Compounds Nos. 16 and 17.

The compounds of the present invention show excellent activities as active ingredients for insecticides, miticides, nematocides and soil pesticides. For instance, they are effective against plant parasitic mites such as two-spotted spider mite (*Tetranychus urticae*), carmine spider mite (*Tetranychus cinnabarinus*), citrus red mite (*Panonychus citri*) or bulb mite (*Rhizoglyphus echinopus*); agricultural insect pests such as diamondback moth (*Plutella xylostella*), cabbage armyworm (*Mamestra brassicae*), common cutworm (*Spodoptera litura*), colorado potato beetle (*Leptinotarsa decemlineata*), codling moth (*Laspeyresia pomonella*), bollworm (*Heliothis zea*), tobacco budworm (*Heliothis virescens*), boll weevil (*Anthonomus grandis*), gypsy moth (*Lymantria dispar*), cucurbit leaf beetle (*Aulacophora femoralis*), aphids, planthoppers, leafhoppers, scales, bugs, whiteflies, thrips, grasshoppers, anthomyiid flies, scarabs, black cutworm (*Agrotis ipsilon*) cutworm (*Agrotis segetum*) or ants; hygienic insect pests such as tropical rat mite (*Ornithonyssus bacoti*), cockroaches, housefly (*Musca domestica*) or house mosquito (*Culex pipiens pallens*); stored grain insect pests such as angoumois grain moth (*Sitotroga cerealella*), azuki bean weevil (*Callosobruchus chinensis*), confused flour beetle (*Tribolium confusum*) or mealworms; household goods insect pests such as casemaking clothes moth (*Tinea pellionella*), black carpet beetle (*Anthrenus scrophularidae*) or subterranean termites; and other parasites on domestic animals such as fleas, lice or flies. Further, they are also effective against plant parasitic nematodes such as root-knot nematodes, cyst nematodes, root-lesion nematodes, rice white-tip nematode (*Aphelenchoides besseyi*), strawberry bud nematode (*Nothotylenchus acris*) or pine wood nematode (*Bursaphelenchus lignicolus*). Furthermore, they are effective also against the soil pests. The soil pests in the present invention are gastropods such as slugs or snails, or isopods such as pillbugs or sowbugs. Still further, they are effective also against mites having the resistance to dicofol and organophosphorus insecticides and against insect pests such as aphids and housefly having the resistance to organophosphorus insecticides. Moreover, the compounds of the present invention have excellent systemic properties, and by the application of the compounds of the present invention to soil treatment, not only noxious insects, noxious mites, noxious nematodes, noxious gastropods and noxious isopods in soil but also foliage pests can be controlled.

When used as active ingredients for insecticides, miticides, nematicides or soil pesticides, the compounds of the present invention may be formulated together with agricultural adjuvants into various forms such as dusts, granules, wettable powders, emulsifiable concentrates, dispersions, aerosols or pastes, just like conventional agricultural chemicals. When such formulations are to be actually used, they may be used as they are or after being diluted with suitable diluents such as water to a predetermined concentration.

Such formulations are usually composed of 0.5–90 parts by weight of active ingredient and 10–99.5 parts by weight of agricultural adjuvants.

As the agricultural adjuvants, there may be mentioned carriers, emulsifiers, suspending agents, dispersants, extenders, penetrating agents, wetting agents, thickeners or stabilizers. They may be added as the case requires. The carriers may be divided into solid carriers and liquid carriers. As the solid carriers, there may be mentioned powders of animal and plant origin, such as starch, activated carbon, soybean flour, wheat flour, wood powder, fish powder or powdered milk; or mineral powders such as talc, kaolin, bentonite, calcium carbonate, zeolite, diatomaceous earth, white carbon, clay, alumina or sulfur powder. As the liquid carriers, there may be mentioned water; alcohols such as methyl alcohol or ethylene glycol; ketones such as acetone or methyl ethyl ketone; ethers such as dioxane or tetrahydrofuran; aliphatic hydrocarbons such as kerosine or the like; aromatic hydrocarbons such as xylene, trimethylbenzene, tetramethylbenzene, cyclohexane or solvent naphtha; halogenated hydrocarbons such as chloroform or chlorobenzene; acid amides such as dimethylformamide; esters such as ethyl acetate or glycerine ester of a fatty acid; nitriles such as acetonitrile; or sulfur-containing compounds such as dimethyl sulfoxide.

Further, the compounds of the present invention may be used in combination with other agricultural chemicals such as insecticides, miticides, nematicides, fungicides, antiviral agents, attractants, herbicides or plant growth regulators, as the case requires. In some cases, the effectiveness will be improved by such combination.

For instance, as such insecticides, miticides or nematicides, there may be mentioned organophosphorus compounds such as O-(4-bromo-2-chlorophenyl) O-ethyl S-propyl phosphorothioate, 2,2-dichlorovinyl dimethyl phosphate, ethyl 3-methyl-4-(methylthio)phenyl isopropylphosphoramidate, O,O-dimethyl O-4-nitro-m-tolyl phosphorothioate, O-ethyl O-4-nitrophenyl phenylphosphonothioate, O,O-diethyl O-2-isopropyl-6-methylpyrimidin-4-yl phosphorothioate, O,O-dimethyl O-(3,5,6-trichloro-2-pyridyl) phosphorothioate, O,S-dimethyl acetylphosphoramidothioate or O-(2,4-dichlorophenyl) O-ethyl S-propyl phosphorodithioate; carbamate compounds such as 1-naphthyl methylcarbamate, 2-isopropoxyphenyl methylcarbamate, 2-methyl-2(methylthio)propionaldehyde O-methylcarbamoyloxime, 2,3-dihydro-2,2-dimethylbenzofuran-7-yl methylcarbamate, dimethyl N,N'-[thiobis {(methylimino)carbonyloxy}] bisethanimidothioate, S-methyl N-(methylcarbamoyloxy) thioacetoimidate, N,N-dimethyl-2-methylcarbamoyloxy- imino-2-(methylthio)acetamide, 2-(ethylthiomethyl)phenyl methylcarbamate, 2-dimethylamino-5,6-dimethyl-pyrimidin-4-yl dimethylcarbamate or S,S'-2-dimethyl aminotrimethylene bis(thiocarbamate); organic chlorine compounds such as 2,2,2-trichloro-1,1-bis(4chlorophenyl)ethanol or 4-chlorophenyl-2,4,5-trichlorophenyl sulfone; organic metal compounds such as tricyclohexyltin hydroxide; pyrethroide compounds such as (RS)-α-cyano-3-phenoxybenzyl (RS)-2-(4-chlorophenyl)-3-methylbutyrate, 3-phenoxybenzyl (1RS)-cis,trans-3-(2,2-dichlorovinyl)-2,2-dimethylcyclopropanecarboxylate, (RS)-α-cyano-3-phenoxybenzyl (1RS)-cis,trans-3-(2,2-dichlorovinyl)-2,2-dimethylcyclopropanecarboxylate, (S)-α-cyano-3-phenoxybenzyl (1R)-cis-3-(2,2-dibromo-vinyl)-2,2-dimethylcyclopropanecarboxylate, (RS)-α-cyano-3-phenoxybenzyl (1RS)-cis,trans-3-(2-chloro-3,3,3-trifluoropropenyl)-2,2-dimethylcyclopropanecarboxylate or 4-methyl-2,3,5,6-tetrafluorobenzyl-3-(2-chloro-3,3,3-trifluoro-1-propene-1-yl)-2,2-dimethylcyclopropane carboxylate; benzoyl urea compounds such as 1-(4-chlorophenyl)-3-(2,6-difluorobenzoyl)urea, 1-[3,5-dichloro-4-(3-chloro-5-trifluoromethyl-2-pyridyloxy)-phenyl]-3-(2,6-difluorobenzoyl)urea or 1-(3,5-dichloro-2,4-difluorophenyl)-3-(2,6-difluorobenzoyl)urea; other compounds such as 2-tert-butylimino-3-isopropyl-5-phenyl-3,4,5,6-tetrahydro-2H-1,3,5,-thiadiazin-4-one, trans-(4-chlorophenyl)-N-cyclohexyl-4-methyl-2-oxo-thiazolizinon-3-carboxamide N-methylbis(2,4-xylyliminomethyl)amine or N'-(4-chloro-o-tolyl)-N,N-dimethylformamidine; juvenile hormone-like compounds such as isopropyl-(2E,4E)-11-methoxy-3,7,11-trimethyl-2,4-dodecadienoate; and other compounds such as dinitro compounds, organic sulfur compounds, urea compounds or triazine compounds. Further, microbial insecticide such as Bacillus thurigiensis agent or nuclear polyhedrosis virus may also be used in combination with the compounds of the present invention.

As the fungicides, there may be mentioned organophosphorus compounds such as S-benzyl O,O-diisopropyl phosphorothioate, O-ethyl S,S-diphenyl phosphorodithioate or aluminium ethyl hydrogen phosphonate; organic chlorine compounds such as 4,5,6,7-tetrachlorophthalide or tetrachloro-isophthalonitrile; dithiocarbamate compounds such as polymeric manganese ethylenebis(dithiocarbamate), polymeric zinc ethylenebis(dithiocarbamate), manganese ethylenebis(dithiocarbamate) complex with zinc salt, dizinc bis(dimethyldithiocarbamate)-ethylenebis(dithiocarbamate) or polymeric zinc propylenebis(dithiocarbamate); N-halogenothioalkyl compounds such as 3a,4,7,7a-tetrahydro-N-(trichloromethansulfenyl)phthalimide, 3a,4,7,7a-tetrahydro-N-(1,1,2,2-tetrachloroethansulfenyl)phthalimide, or N-(trichloromethylsulfenyl)phthalimide; dicarboxy imide compounds such as 3-(3,5-dichlorophenyl)-N-isopropyl-2,4-dioxoimidazolidine-1-carboxamide, (RS)-3-(3,5-dichlorophenyl)-5-methyl-5-vinyl-1,3-oxazolidine-2,4-dione or N-(3,5-dichlorophenyl)-1,2-dimethylcyclopropane-1,2-dicarboximide; benzimidazole compounds such as methyl 1-(butylcarbamoyl)benzimidazole-2-yl-carbamate or dimetyl 4,4'-(o-phenylene)bis(3-thioallophanate); azole compounds such as 1-(4-chlorophenoxy)-3,3-dimethyl-1-(1H-1,2,4-triazol-1-yl)butanone, 1-(biphenyl-4-yloxy)-3,3-dimethyl-1-(1H-1,2,4-triazol-1-yl) butan-2-ol, 1-[N-(4-chloro-2-trifluoromethylphenyl)-2-propoxyacetoimidoyl]imidazole, 1-[2-(2,4-dichlorophenyl)-4-ethyl-1, 3-dioxolan-2ylmethyl]1H-1,2,4-triazole, 1-[2-(2,4-dichlorophenyl)-4-propyl-1,3-dioxolan-2-ylmethyl]-1H-1,2,4triazole or 1-[2-(2,4-dichlorophenyl)pentyl]-1H-1,2,4-triazole; carbinol compounds such as (±)-2,4'-dichloro-α-(pyrimidin-5-yl)benzhydryl alcohol or 2,4'-difluoro-α-(1H-1,2,4-triazol-1-ylmethyl) benzhydryl alcohol; benzanilide compounds such as 3'-isopropoxy-o-toluanilide or α,α,α-trifluoro-3'-isopropoxy-o-toluanilide; acylalanine compounds such as methyl N-(2-methoxyacetyl)-N-(2,6-xylyl)-DL-alaninate; pyridinamine compounds such as 3-chloro-N-(3-chloro-2,6-dinitro-4-α,α,α-trifluorotolyl)-5-trifluoromethyl-2-pyridinamine; and other compounds such as piperazine compounds, morpholine compounds, anthraquinone compounds, quinoxaline compounds, crotonic acid compounds, sulfenic acid compounds, urea compounds or antibiotic substances.

The insecticides, miticides, nematicides and soil pesticides of the present invention are effective for the control of various noxious soil insects, noxious mites, noxious nematodes and noxious pests. They are applied in an active ingredient concentration of from 1 to 20,000 ppm, preferably from 20 to 2,000 ppm. The active ingredient concentration may be optionally changed depending upon the formulation, the manner, purpose, timing or place of the application and the condition of the insect pests. For instance, aquatic noxious insects can be controlled by applying the formulation having the above-mentioned concentration to the site of the outbreak, and thus, the concentration of the active ingredient in water is less than the above-mentioned range.

The amount of the application of the active ingredient per unit surface area is usually from about 0.1 to 5,000 g, preferably from 10 to 1,000 g, per 10a. However, in a certain special case, the amount of the application may be outside the above range.

Various formulations containing the compounds of the present invention or their diluted compositions may be applied by conventional methods for application which are commonly employed, such as spraying (e.g. spraying, jetting, misting, atomizing, powder or grain scattering or dispersing in water), soil application (e.g. mixing or drenching), surface application (e.g. coating, powdering or covering) or impregnation to obtain poisonous feed. Further, it is possible to feed domestic animals with a feed containing the above active ingredient and to control the outbreak or growth of pests, particularly insect pests, with their excrements. Furthermore, the active ingredient may also be applied by a so-called ultra low-volume application method. In this method, the composition may be composed of 100% of the active ingredient.

TEST EXAMPLE 1

Each of formulations containing the active ingredients (Compounds Nos. 1 to 32) was dispersed in water to obtain a dispersion of each active ingredient having concentration of 800 ppm. Each of French bean seedlings with only one primary leaf left, was transplanted to a cup having a diameter of 7 cm and a height of 4 cm. About 30 nimphs and adults of two-spotted spider mite (*Tetranychus urticae*) were infested to the leaf of the French bean. Then, the French bean was dipped in the dispersion having the concentration of 800 ppm for about 10 seconds, then dried in air and kept in a constant temperature chamber with lightening at 26° C. At two days after the treatment, dead mites were counted, and the mortality was calculated by the following equation:

$$\text{Mortality }(\%) = \frac{\text{Number of dead mites}}{\text{Number of total mites}} \times 100$$

The mortality was 100% with respect to each of Compounds Nos. 1 to 32.

TEST EXAMPLE 2

Each of formulations containing the active ingredients identified in Table 3, was dispersed in water to obtain dispersions of each active ingredient having concentrations of 800 ppm and 200 ppm. Leaves of cabbage were dipped in the respective dispersions for about 10 seconds, and then dried in air. A sheet of moistened filter paper was placed in a Petri dish having a diameter of 9 cm, and the dried leaves of cabbage were put on the filter paper. Larvae of diamondback moth (*Plutella xylostella*) in second or third instar were released on the leaves, and the Petri dishes were covered and kept in a constant temperature chamber with lightening at a temperature of 26° C. At two days after released, dead insects were counted, and the mortality was calculated by the following equation:

$$\text{Mortality }(\%) = \frac{\text{Number of dead insects}}{\text{Number of total insects}} \times 100$$

The results are shown in Table 3.

TABLE 3

| Compound No. | Mortality (%) 800 ppm of active ingredient | Mortality (%) 200 ppm of active ingredient | Compound No. | Mortality (%) 800 ppm of active ingredient | Mortality (%) 200 ppm of active ingredient |
| --- | --- | --- | --- | --- | --- |
| 1 | 100 | — | 20 | 100 | 100 |
| 2 | 100 | 70 | 21 | 100 | 100 |
| 3 | 100 | 100 | 22 | 100 | 90 |
| 4 | 100 | 100 | 23 | 100 | 80 |
| 5 | 100 | 100 | 24 | 100 | 100 |
| 6 | 100 | 100 | 25 | 100 | 70 |
| 7 | 100 | 100 | 26 | 100 | 100 |
| 8 | 100 | 100 | 27 | 100 | 70 |
| 9 | 100 | 100 | 28 | 100 | 90 |
| 10 | 100 | 100 | 29 | 100 | 100 |
| 11 | 100 | 100 | 30 | 100 | 100 |
| 15 | 100 | 100 | 31 | 100 | 100 |
| 18 | 100 | 100 | 32 | 100 | 100 |
| 19 | 100 | 100 | | | |

TEST EXAMPLE 3

The tests were conducted in the same manner as in Test Example 2 except that larvae of common cutworm (*Spodoptera litura*) in second or third instar were used instead of larvae of the diamondback moth in second or third instar. The results are shown in Table 4.

TABLE 4

| Compound No. | Mortality (%) 800 ppm of active ingredient | Mortality (%) 200 ppm of active ingredient | Compound No. | Mortality (%) 800 ppm of active ingredient | Mortality (%) 200 ppm of active ingredient |
| --- | --- | --- | --- | --- | --- |
| 1 | 100 | 100 | 20 | 100 | 100 |
| 2 | 100 | 90 | 21 | 100 | — |
| 3 | 100 | 100 | 23 | 100 | 100 |
| 4 | 100 | 100 | 24 | 100 | 100 |
| 5 | 100 | 100 | 25 | 100 | 90 |
| 6 | 100 | 100 | 26 | 100 | 90 |
| 7 | 100 | 100 | 28 | 100 | 90 |
| 8 | 90 | — | 29 | 100 | 100 |
| 9 | 100 | 90 | 30 | 100 | 100 |
| 10 | 100 | 100 | 31 | 100 | 100 |
| 11 | 100 | 100 | 32 | 100 | 90 |
| 12 | 90 | — | | | |
| 15 | 100 | 100 | | | |
| 18 | 100 | 100 | | | |
| 19 | 100 | 100 | | | |

TEST EXAMPLE 4

Each of French bean seedlings with only one primary leaf left, was transplanted to a cup (same as Test Example 1). Adults of two-spotted spider mite (Tetranychus urticae) were infested to the leaf of the French bean and permitted to lay eggs, and then the adults were removed. Then, the French bean was dipped for about 10 seconds in a dispersion prepared by dispersing each of formulations containing the active ingredients identified in Table 5, in water to obtain a concentration of 800 ppm as the active ingredient. Then, the French bean was dried in air, and kept in a constant temperature chamber with lightening at 26° C. At five days after the treatment, the hatching of eggs was examined, and the dead egg rate was calculated by the following equation:

$$\text{Dead egg rate (\%)} = \frac{\text{Number of dead eggs}}{\text{Number of total eggs}} \times 100$$

The results are shown in Table 5. Moreover, the number of dead nimphs which had just hatched was regarded as the number of dead eggs.

TABLE 5

| Compound No. | Dead egg rate (%) 800 ppm of active ingredient | Compound No. | Dead egg rate (%) 800 ppm of active ingredient |
| --- | --- | --- | --- |
| 1 | 83 | 23 | 100 |
| 6 | 90 | 24 | 100 |
| 8 | 94 | 25 | 100 |
| 9 | 94 | 26 | 100 |
| 12 | 100 | 27 | 100 |
| 13 | 100 | 28 | 100 |
| 14 | 100 | 29 | 100 |
| 20 | 100 | 30 | 100 |
| 22 | 82 | 31 | 100 |

TEST EXAMPLE 5

A rice seedling was dipped in a dispersion containing a predetermined concentration of each active ingredient for 10 seconds, then dried in air and put into a test tube with the root portion enclosed by absorbent cotton. Then, 10 adults of brown rice planthopper (Nilaparvata lugens) were released in the test tube, and the mouth of the test tube was covered with a gauze. Then, the test tube was kept in a constant temperature chamber with lightening at 26° C. At two days after the release, dead insects were counted, and the mortality was calculated in the same manner as in Test Example 2. The results are shown in Table 6.

TABLE 6

| Compound No. | Mortality (%) 800 ppm of active ingredient | Mortality (%) 200 ppm of active ingredient | Compound No. | Mortality (%) 800 ppm of active ingredient | Mortality (%) 200 ppm of active ingredient |
| --- | --- | --- | --- | --- | --- |
| 1 | 100 | — | 18 | 100 | 100 |
| 2 | 100 | 100 | 19 | 100 | 100 |
| 3 | 100 | 90 | 20 | 100 | 100 |
| 4 | 100 | 100 | 21 | 100 | 100 |
| 5 | 100 | 100 | 22 | 100 | 100 |
| 6 | 100 | — | 23 | 100 | — |
| 7 | 100 | 100 | 25 | 100 | 90 |
| 8 | 100 | — | 27 | 100 | 80 |
| 9 | 100 | — | 28 | 100 | — |
| 10 | 100 | 80 | 29 | 100 | 90 |
| 11 | 100 | 100 | 30 | 100 | 90 |
| 13 | 100 | 100 | 31 | 100 | — |
| 14 | 100 | 100 | 32 | 90 | 80 |
| 15 | 100 | 100 | | | |

TEST EXAMPLE 6

The soil contaminated by southern root-knot nematode (*Meloindgyne incognitay*) was put in a pot of 1/14,000a., and a dispersion containing an active ingredient was poured into the pot to bring the concentration of the active ingredient to 80 g/a. At two days after the treatment, the treated soil was mixed, and a tomato seedling in 3- or 4-leaf stage was transplanted in the pot. At twenty days after the treatment of the active ingredient, the root-gall index was investigated. The results are shown in Table 7. The root-gall index was determined based on the following standards:

0: No galls
1: 1–25% of roots galled
2: 26–50% of roots galled
3: 51–75% of roots galled
4: 76–100% of roots galled

TABLE 7

| Compound No. | Root-gall index | Compound No. | Root-gall index | Compound No. | Root-gall index |
|---|---|---|---|---|---|
| 1 | 0 | 12 | 0 | 24 | 0 |
| 2 | 0 | 13 | 0 | 25 | 0 |
| 3 | 0 | 14 | 0 | 26 | 0 |
| 4 | 0 | 15 | 0 | 27 | 0 |
| 5 | 0 | 18 | 0 | 28 | 0 |
| 6 | 1 | 19 | 0 | 29 | 0 |
| 7 | 0 | 20 | 0 | | |
| 8 | 1 | 21 | 0 | | |
| 9 | 0 | 22 | 0 | | |
| 10 | 0 | 23 | 0 | | |

TEST EXAMPLE 7

Each of formulations containing active ingredients, was dispersed in water to obtain a dispersion having a predetermined concentration. Leaves of cabbage were dipped in the dispersion for about 10 seconds, and then dried in air. A sheet of moistened filter paper was placed in a Petri dish having a diameter of 9 cm, and the dried leaves of cabbage were put on the sheet. Apterous viviparous females of green peach aphid (*Myzus persicae*) were released on the leaves, and the Petri dish was covered and kept in a constant temperature chamber with lightening at 26° C. At two days after the release, dead insects were counted, and the mortality was calculated in the same manner as in Test Example 2. The results are shown in Table 8.

TABLE 8

| Compound No. | Mortality (%) 800 ppm of active ingredient | Mortality (%) 200 ppm of active ingredient | Compound No. | Mortality (%) 800 ppm of active ingredient | Mortality (%) 200 ppm of active ingredient |
|---|---|---|---|---|---|
| 1 | 100 | 80 | 19 | 100 | 100 |
| 2 | 100 | 100 | 20 | 100 | 100 |
| 3 | 100 | 100 | 21 | 100 | 100 |
| 4 | 100 | 100 | 22 | 100 | 100 |
| 5 | 100 | 100 | 23 | — | 100 |
| 6 | 100 | 100 | 24 | 100 | 100 |
| 7 | 100 | 100 | 25 | 100 | 100 |
| 8 | 100 | 100 | 26 | 100 | 100 |
| 9 | 100 | 100 | 27 | 100 | 100 |
| 10 | 100 | 100 | 28 | 100 | 100 |
| 11 | 100 | 100 | 29 | 100 | 100 |
| 12 | 100 | — | 30 | 100 | 80 |
| 13 | 100 | — | 31 | — | 90 |
| 15 | 100 | 100 | 32 | 100 | 100 |
| 18 | 100 | 100 | | | |

TEST EXAMPLE 8

Each of formulations containing the active ingredients identified in Table 9, was dispersed in water to obtain a dispersion having a predetermined concentration. Each of French bean seedlings with only one primary leaf left, was transplanted to a cup (same as the Test Example 1), and about 30 nimphs and adults of two-spotted spider mite (*Tetranychus urticae*) having the resistance to dicofol and organophosphorus insecticides, were infested to the French bean. Then, the French bean was dipped in the dispersion having the above-mentioned predetermined concentration for about 10 seconds, then dried in air and kept in a constant temperature chamber with lightening at a temperature of 26° C. At two days after the treatment, the dead mites were counted, and the mortality was calculated in the same manner as in Test Example 1. The results are shown in Table 9.

TABLE 9

| Compound No. | Mortality (%) 100 ppm of active ingredient | Mortality (%) 50 ppm of active ingredient | Compound No. | Mortality (%) 100 ppm of active ingredient | Mortality (%) 50 ppm of active ingredient |
|---|---|---|---|---|---|
| 1 | 100 | — | 14 | 100 | 79 |
| 3 | 100 | 100 | 15 | 100 | 100 |
| 4 | 100 | 100 | 18 | 100 | 100 |
| 5 | 100 | 89 | 19 | 100 | 96 |
| 8 | 92 | — | 22 | 95 | 62 |
| 9 | 96 | 82 | 24 | 100 | 98 |
| 10 | 100 | 100 | 25 | 100 | 86 |
| 11 | 91 | 97 | 28 | 100 | 100 |
| 13 | 100 | 80 | | | |
| | | | Dicofol (Comparative) | 85 | 10 |
| | | | ESP (Comparative) | 0 | 0 |

TEST EXAMPLE 9

Each of formulations containing the active ingredients identified in Table 10, was dispersed in water to obtain a dispersion containing 800 ppm of the active ingredient. Each of French bean seedlings having two primary leaves, was transplanted to a cup (same as the Test Example 1), and 10 ml of the dispersion having the above-mentioned concentration was applied by soil drenching. At two days after the treatment, about 30 nimphs and adults of two-spotted spider mite (*Tetranychus urticae*) having the resistance to dicofol and organophosphorus insecticides, were infested to the leaves, and the cup was kept in a constant temperature chamber with lightening at 26° C. At two days after infestation, the dead mites were counted, and the mortality was calculated in the same manner as in Test Example 1. The results are shown in Table 10.

TABLE 10

| Compound No. | Mortality rate (%) | Compound No. | Mortality rate (%) |
|---|---|---|---|
| 1 | 100 | 20 | 100 |
| 3 | 100 | 21 | 100 |
| 4 | 100 | 22 | 100 |
| 5 | 100 | 24 | 98 |
| 7 | 100 | 25 | 100 |
| 10 | 100 | 27 | 100 |
| 11 | 100 | 28 | 100 |
| 15 | 100 | 29 | 100 |
| 18 | 100 | 30 | 100 |
| 19 | 80 | 31 | 84 |

TEST EXAMPLE 10

40 g of dried soil was put into an icecream cup, and 10 ml of a dispersion of 500 ppm of an active ingredient, was poured to the soil. The soil was uniformly mixed. Twenty-four hours later, an onion piece as feed was put in the soil, and 10 larvae of onion maggot (*Hylemya antiqua*) of 10 days old were released on the soil, and the cup was kept in a constant temperature chamber with lightening at 26° C. At forty-eight hours after the release, the dead insects were counted, and the mortality was calculated in the same manner as in Test Example 2. The results are shown in Table 11.

TABLE 11

| Compound No. | Mortality rate (%) | Compound No. | Mortality rate (%) |
|---|---|---|---|
| 2 | 100 | 10 | 100 |
| 3 | 100 | 12 | 100 |
| 4 | 100 | 14 | 100 |
| 5 | 100 | 15 | 100 |
| 6 | 100 | 18 | 100 |
| 7 | 100 | 24 | 100 |
| 8 | 100 | 25 | 100 |
| 9 | 100 | | |

TEST EXAMPLE 11

Tests were conducted in the same manner as in Test Example 7 except that green peach aphid (*Myzus persicae*) having the resistance to organophosphorus insecticides was used instead of ordinary green peach aphid. The results are shown in Table 12.

TABLE 12

| Compound No. | Mortality rate (%) 800 ppm of active ingredient |
|---|---|
| 7 | 100 |
| 9 | 100 |
| 15 | 100 |
| 18 | 100 |
| 20 | 100 |
| 21 | 100 |
| 25 | 100 |
| 27 | 100 |
| Fenitrothion (Comparative) | 0 |
| Dimethoate (Comparative) | 20 |
| Diazinon (Comparative) | 30 |

TEST EXAMPLE 12

Powder feed for test animals (manufactured by Oriental Kobo Kogyo K.K.) and bran were mixed in a weight ratio of 1:1 and pulverized, and 10 g of the mixture was packed in an ice cream cup. Each of the formulations containing the active ingredients, was dispersed in water, and 10 ml of the dispersion was added to the mixture in the ice cream cup and thoroughly mixed to adjust the concentration of the active ingredient to 100 ppm or 50 ppm. Into the ice cream cup, 20 larvae of house fly (*Musca domestica*, No. 3 Yume-no-shima colony) of three days old having the resistance to organophosphorus insecticides were released, and kept in a constant temperature chamber with lightening at 26° C. Sixth day after the release, the recovered purpae were counted, and the mortality was calculated in accordance with the following equation. The results are shown in Table 13.

$$\text{Mortality (\%)} = \frac{\text{Number of Released larvae} - \text{Number of Recovered purpae}}{\text{Number of Released larvae}} \times 100$$

TABLE 13

| Compound No. | Mortality (%) 100 ppm of active ingredient | Mortality (%) 50 ppm of active ingredient | Compound No. | Mortality (%) 100 ppm of active ingredient | Mortality (%) 50 ppm of active ingredient |
|---|---|---|---|---|---|
| 4 | 100 | 100 | 19 | 100 | 90 |
| 7 | 100 | 100 | 20 | 100 | 100 |
| 12 | 100 | 100 | | | |
| 15 | 100 | 100 | | | |
| 18 | 100 | 100 | Fenitrothion (Comparative) | 45 | 30 |

TEST EXAMPLE 13

Tests were conducted in the same manner as in Test Example 10 except that the larvae of onion maggot of 10 days old were replaced by pillbug (*Armadillidium vulgare*), the examination after 48 hours was changed to an examination after 4 days, and no onion piece as feed was used. The results are shown in Table 14.

TABLE 14

| Compound No. | Mortality rate (%) |
|---|---|
| 3 | 100 |
| 9 | 100 |
| 10 | 100 |

TEST EXAMPLE 14

Tests were conducted in the same manner as Test Example 10 except that the concentration of the dispersion was changed from 500 ppm to 20 ppm, the larvae of onion maggot of 10 days old were replaced by larvae of cucurbit leaf beetle (*Aulacophore femoralis*) in second or third instar, the onion piece was replaced by a cucumber piece, and the examination after 48 hours was changed to an examination after 7 days. The results are shown in Table 15.

TABLE 15

| Compound No. | Mortality rate (%) | Compound No. | Mortality rate (%) |
|---|---|---|---|
| 4 | 100 | 15 | 100 |
| 5 | 100 | 18 | 100 |
| 7 | 100 | 23 | 100 |
| 9 | 100 | 24 | 100 |
| 10 | 100 | 25 | 100 |
| 14 | 100 | | |

FORMULATION EXAMPLE 1

(a) Compound No. 4: 20 Parts by weight
(b) N,N'-dimethylformamide: 32 Parts by weight (c) xylene: 40 Parts by weight
(d) Polyoxyethylenealkylphenyl ether: 8 Parts by weight The above components are uniformly mixed and dissolved to obtain an emulsifiable concentrate.

FORMULATION EXAMPLE 2

(a) Compound No. 15: 50 Parts by weight
(b) Tetramethylbenzene: 38 Parts by weight
(c) An emulsifier mixture comprising an alkylbenzene sulfonate, a polyoxyethylenealkylphenol ether and a polyoxyethylenephenylphenol ether (Aglysol P-311 (Trade name), manufactured by Kao Soap Co. Ltd.): 12 Parts by weight The above components are uniformly mixed and dissolved to obtain an emulsifiable concentrate.

FORMULATION EXAMPLE 3

(a) Compound No. 20: 85 Parts by weight
(b) The emulsifier mixture as used in Formulation Example 2: 15 Parts by weight The above components are uniformly mixed to obtain a highly concentrated emulsifiable concentrate.

FORMULATION EXAMPLE 4

(a) Compound No. 18: 5 Parts by weight
(b) Talc: 95 Parts by weight

The above components are uniformly mixed to obtain a dust.

FORMULATION EXAMPLE 5

(a) Compound No. 12: 5 Parts by weight
(b) Bentonite: 45 Parts by weight
(c) Kaoline: 50 Parts by weight The above components are kneaded together with a small amount of water, then extruded in a granular form and dried to obtain granules.

FORMULATION EXAMPLE 6

(a) Compound No. 13: 0.50 Part by weight
(b) Polyoxyethyleneoctylphenyl ether: 0.15 Part by weight
(c) Polyoxyethylene phosphate: 0.10 Part by weight
(d) White carbon: 1.00 Part by weight
(e) Granular calcium carbonate: 98.25 Parts by weight Components (a) to (c) are preliminarily uniformly mixed, then diluted with a proper amount of acetone, and then sprayed on component (e), and then acetone was removed, and then mixed (d) uniformly to obtain granules.

FORMULATION EXAMPLE 7

(a) Compound No. 28: 50 Parts by weight
(b) Fine silica powder: 15 Parts by weight
(c) Fine clay powder: 25 Parts by weight
(d) A condensation product of sodium naphthalene-sulfonate with formalin: 2 Parts by weight
(e) Dialkyl sulfosuccinate: 3 Parts by weight
(f) Polyoxyethylenealkylallyl ether sulfate: 5 Parts by weight The above components are uniformly pulverized and mixed to obtain a wettable powder.

FORMULATION EXAMPLE 8

(a) Compound No. 9: 5 Parts by weight
(b) Glycerin: 5 Parts by weight
(c) Milk powder: 3 Parts by weight
(d) Fish powder: 87 Parts by weight The above components are uniformly kneaded to obtain a paste.

FORMULATION EXAMPLE 9

(a) Compound No. 9: 10 Parts by weight
(b) Polyoxyethyleneoctylphenyl ether: 3 Parts by weight
(c) Kerosine: 87 Parts by weight The above components are uniformly mixed and dissolved to obtain an aerosol to be sprayed by compressed air.

FORMULATION EXAMPLE 10

(a) Compound No. 30: 5 Parts by weight
(b) An emulsifier mixture comprising a polyethylene phenylphenol derivative, a polyethylene alkylaryl ether, a polyethylene sorbitan alkylate and an alkylaryl sulfonate (Sorpol 2806 (Trade name), manufactured by Tono Chemical Co. Ltd.): 5 Parts by weight
(c) xylene: 90 Parts by weight The above components are uniformly mixed and dissolved to obtain an emulsifiable concentrate.

FORMULATION EXAMPLE 11

(a) Compound No. 14: 20 Parts by weight
(b) Dialkyl sulfosuccinate (Na salt): 3 Parts by weight
(c) Polyethylene octylphenyl ether: 6 Parts by weight
(d) Diatomacious earth (Granules): 71 Parts by weight Components (a) to (c) are preliminarily uniformly mixed and sprayed on component (d) to obtain granules.

FORMULATION EXAMPLE 12

(a) Compound No. 7: 1 Part by weight
(b) Talc: 99 Parts by weight

The above components are uniformly mixed to obtain a dust.

FORMULATION EXAMPLE 13

(a) Compound No. 32: 10 Parts by weight
(b) White carbon: 5 Parts by weight
(c) Clay: 75 Parts by weight
(d) Naphthalene sulfonic acid condensate with formaldehyde: 2 Parts by weight
(e) Dialkyl sulfosuccinate: 3 Parts by weight
(f) Polyethylene alkylarylether: 5 Parts by weight The above components are uniformly pulverized and mixed to obtain a wettable powder.

We claim:

1. An organophosphorus compound having the formula:

$$\begin{array}{c} X_1 \\ X_2 \end{array} \begin{array}{c} Y_2 \\ \| \\ N-P \end{array} \begin{array}{c} Y_3R_1 \\ SR_2 \end{array} \quad (I)$$

$$Z \diagdown_N \diagup^{Y_1}$$
$$\quad |$$
$$\quad X_3$$

wherein each of $X_1$, $X_2$ and $X_3$ is a hydrogen atom; an alkyl, alkoxy or alkenyl group which may be substituted by halogen, alkoxy, alkylthio, cycloalkyl or phenyl; or a cycloalkyl group, each of $Y_1$, $Y_2$ and $Y_3$ is an oxygen atom or a sulfur atom, Z is a carbonyl group; and each of $R_1$ and $R_2$ is an alkyl group which may be substituted by halogen, alkoxy or alkylthio.

2. The compound according to claim 1, wherein each of $Y_2$ and $Y_3$ is an oxygen atom.

3. The compound according to claim 1, wherein each of $R_1$ and $R_2$ is an alkyl group.

4. The compound according to claim 1, wherein $X_3$ is a hydrogen atom; an alkyl or alkoxy group which may be substituted by phenyl; or a cycloalkyl group.

5. The compound according to claim 1, wherein each of $X_1$ and $X_2$ is a hydrogen atom, an alkyl group or an alkoxy group.

6. The compound according to claim 1, wherein $Y_1$ is an oxygen atom.

7. The compound according to claim 1, wherein $X_3$ is a hydrogen atom, an alkyl group or a cycloalkyl group.

8. The compound according to claim 1, wherein each of $X_1$ and $X_2$ is a hydrogen atom, an alkyl group or an alkoxy group, $X_3$ is an alkyl group, each of $Y_1$, $Y_2$ and $Y_3$ is an oxygen atom, Z is a carbonyl group, and each of $R_1$ and $R_2$ is an alkyl group.

9. The compound according to claim 8, wherein $R_1$ is a methyl group or an ethyl group, and $R_2$ is a n-propyl group, an isopropyl group, a n-butyl group, a sec-butyl group, an isobutyl group or a tert-butyl group.

10. The compound according to claim 8, wherein $R_1$ is an ethyl group, and $R_2$ is a n-propyl group or a sec-butyl group.

11. The compound according to claim 10, which is O-ethyl S-n-propyl (3-methyl-2,4-dioxo-1-imidazolidinyl) phosphonothiolate.

12. The compound according to claim 10, which is S-sec-butyl O-ethyl (3-methyl-2,4-dioxo-1-imidazolidinyl) phosphonothiolate.

13. The compound according to claim 10, which is S-sec-butyl O-ethyl (3-isopropyl-2,4-dioxo-1-imidazolidinyl) phosphonothiolate.

14. The compound according to claim 10, which is S-sec-butyl O-ethyl (5-ethyl-3-methyl-2,4-dioxo-1-imidazolidinyl)phosphonothiolate.

15. The compound according to claim 10, which is S-sec-butyl O-ethyl (3-ethyl-5,5-dimethyl-2,4-dioxo-1-imidazolidinyl)phosphonothiolate.

16. The compound according to claim 10, which is S-sec-butyl O-ethyl (3,5-dimethyl-2,4-dioxo-1-imidazolidinyl) phosphonothiolate.

17. The compound according to claim 10, which is S-sec-butyl O-ethyl (5-sec-butyl-3-methyl-2,4-dioxo-1-imidazolidinyl)phosphonothiolate.

18. The compound according to claim 10, which is S-sec-butyl O-ethyl (3-methyl-5-isopropyl-2,4-dioxo-1-imidazolidinyl)phosphonothiolate.

19. The compound according to claim 10, which is S-sec-butyl O-ethyl (5-ethyl-5-methyl-2,4-dioxo-1-imidazolidinyl)phosphonothiolate.

20. The compound according to claim 10, which is S-sec-butyl O-ethyl (2,4-dioxo-1-imidazolidinyl)phosphonothiolate.

21. The compound according to claim 10, which is S-sec-butyl O-ethyl (5,5-dimethyl-2,4-dioxo-1-imidazolidinyl) phosphonothiolate.

22. An insecticidal, miticidal, nematicidal or soil pesticidal composition comprising an insecticidally, miticidally, nematicidally or soil pesticidally effective amount of an organophosphorus compound of the formula I as defined in claim 1 and a carrier.

23. An insecticidal, miticidal, nematicidal or soil pesticidal method, which comprises applying an insecticidally, miticidally, nematicidally or soil pesticidally effective amount of an organophosphorus compound of the formula I as defined in claim 1 to a site to be protected.

* * * * *